(12) United States Patent
Nassar (10) Patent No.: US 12,324,575 B1
(45) Date of Patent: Jun. 10, 2025

(54) DEVICES AND METHODS FOR CLOSING ABDOMINAL FASCIA AND OTHER INCISIONS

(71) Applicant: THE BOARD OF TRUSTEES OF THE LELAND STANFORD JUNIOR UNIVERSITY, Stanford, CA (US)

(72) Inventor: Aussama K. Nassar, Redwood City, CA (US)

(73) Assignee: The Board of Trustees of the Leland Stanford Jr. University, Stanford, CA (US)

( * ) Notice: Subject to any disclaimer, the term of this patent is extended or adjusted under 35 U.S.C. 154(b) by 547 days.

(21) Appl. No.: 17/549,476

(22) Filed: Dec. 13, 2021

Related U.S. Application Data (63) Continuation of application No. PCT/US2020/037662, filed on Jun. 14, 2020.

(60) Provisional application No. 62/861,908, filed on Jun. 14, 2019.

(51) Int. Cl.
*A61B 17/04* (2006.01)
*A61B 17/00* (2006.01)

(52) U.S. Cl.
CPC ............... *A61B 17/0401* (2013.01); *A61B 2017/00004* (2013.01); *A61B 2017/0406* (2013.01)

(58) Field of Classification Search
CPC ...... A61B 17/0401; A61B 2017/00004; A61B 2017/0406
See application file for complete search history.

(56) References Cited

U.S. PATENT DOCUMENTS

| | | | |
|---|---|---|---|
| 2,104,885 A | * | 1/1938 | Robbins ............ A44B 1/28 24/690 |
| 2,199,025 A | | 4/1940 | Conn |
| 3,541,591 A | | 11/1970 | Hoegerman et al. |
| 3,664,345 A | | 5/1972 | Dabbs et al. |
| 3,716,058 A | | 2/1973 | Tanner, Jr. |
| 3,924,629 A | * | 12/1975 | Akiyama ........ A61B 17/0682 606/158 |
| 4,006,747 A | | 2/1977 | Kronenthal et al. |

(Continued)

FOREIGN PATENT DOCUMENTS

| | | |
|---|---|---|
| WO | 2015012887 A1 | 1/2015 |
| WO | 2016069327 A1 | 5/2016 |
| WO | 2018132801 A1 | 7/2018 |

OTHER PUBLICATIONS

Korean Intellectual Property Office, Authorized officer: Kim, Yeonkyung, International Search Report for corresponding International Application No. PCT/US2020/037662, Oct. 6, 2020, 5 pages.

(Continued)

*Primary Examiner* — Julian W Woo
*Assistant Examiner* — Osama Nemer
(74) *Attorney, Agent, or Firm* — William A. English; Vista IP Law Group LLP (57) ABSTRACT

Devices and methods are provided for closing an incision through fascia or other tissue of a subject. A first closure element is positioned against tissue on a first side of the incision, a second closure element is positioned against tissue on a second side of the incision, and a fastener from or through the first closure element is directed through the tissue and the second closure element to secure the closure elements against the tissue to close the incision.

21 Claims, 7 Drawing Sheets

(56) References Cited

U.S. PATENT DOCUMENTS

| | | | | |
|---|---|---|---|---|
| 4,060,089 | A * | 11/1977 | Noiles | A61B 17/0643 606/220 |
| 4,210,148 | A * | 7/1980 | Stivala | A61B 17/0466 606/232 |
| 4,402,445 | A * | 9/1983 | Green | A61L 31/06 227/77 |
| 4,534,352 | A * | 8/1985 | Korthoff | A61B 17/0643 606/220 |
| 4,610,250 | A * | 9/1986 | Green | A61B 17/0643 606/220 |
| 4,637,380 | A * | 1/1987 | Orejola | A61B 17/08 606/216 |
| 4,805,617 | A * | 2/1989 | Bedi | A61B 17/0643 606/220 |
| 4,823,794 | A | 4/1989 | Pierce | |
| 4,924,864 | A * | 5/1990 | Danzig | A61B 17/122 606/142 |
| 4,994,073 | A * | 2/1991 | Green | A61B 17/064 606/220 |
| 5,000,746 | A | 3/1991 | Meiss | |
| 5,219,359 | A | 6/1993 | McQuilkin et al. | |
| 5,282,829 | A | 2/1994 | Hermes | |
| 5,358,510 | A * | 10/1994 | Luscombe | A61B 17/0643 606/220 |
| 5,843,126 | A * | 12/1998 | Jameel | A61B 17/06 606/220 |
| 5,902,319 | A | 5/1999 | Daley | |
| 7,846,180 | B2 * | 12/2010 | Cerier | A61B 17/068 606/232 |
| 7,972,347 | B2 | 7/2011 | Garvin | |
| 8,313,509 | B2 * | 11/2012 | Kostrzewski | A61B 17/06066 606/232 |
| 8,679,153 | B2 | 3/2014 | Dennis | |
| 8,764,778 | B2 * | 7/2014 | Yeretsian | A61B 17/0644 606/151 |
| 9,011,487 | B2 | 4/2015 | Lindh et al. | |
| 11,730,582 | B2 * | 8/2023 | Felder | A61F 2/0063 606/151 |
| 11,826,041 | B2 * | 11/2023 | Felder | A61B 17/064 |
| 2004/0059377 | A1 * | 3/2004 | Peterson | A61B 17/064 606/216 |
| 2004/0133238 | A1 * | 7/2004 | Cerier | A61B 17/0057 606/232 |
| 2005/0049638 | A1 * | 3/2005 | Mandelbaum | A61F 2/0063 606/215 |
| 2009/0138002 | A1 * | 5/2009 | Fenton | A61B 17/0401 606/232 |
| 2010/0256675 | A1 * | 10/2010 | Romans | A61B 17/0644 606/219 |
| 2011/0068143 | A1 * | 3/2011 | Laufer | A61B 17/0643 227/175.1 |
| 2015/0216527 | A1 * | 8/2015 | Belson | A61B 17/085 606/216 |
| 2015/0351758 | A1 * | 12/2015 | Shelton, IV | A61B 17/07292 606/219 |
| 2016/0081686 | A1 * | 3/2016 | Miksza | A61F 2/0063 606/232 |
| 2016/0120631 | A1 * | 5/2016 | Murphy | A61F 2/0063 606/151 |
| 2016/0310140 | A1 * | 10/2016 | Belson | A61B 5/01 |
| 2019/0059871 | A1 * | 2/2019 | Fischer | A61F 2/0063 |
| 2020/0107826 | A1 | 4/2020 | Kojouri et al. | |

OTHER PUBLICATIONS

Korean Intellectual Property Office, Authorized officer: Kim, Yeonkyung, Written Opinion for corresponding International Application No. PCT/US2020/037662, Oct. 6, 2020, 8 pages.

* cited by examiner

DEVICES AND METHODS FOR CLOSING ABDOMINAL FASCIA AND OTHER INCISIONS

RELATED APPLICATION DATA

The present application is a continuation of co-pending International Application No. PCT/US2020/037662, filed Jun. 14, 2020, which claims benefit of U.S. provisional application Ser. No. 62/861,908, filed Jun. 14, 2019, the entire disclosures of which are expressly incorporated by reference herein.

FIELD OF THE INVENTION

The present invention relates to devices for use during medical procedures, e.g., during open or laparoscopic surgical procedures, and, more particularly, to devices and methods for closing surgical incisions, e.g., through abdominal wall fascia after a laparotomy or laparoscopy.

BACKGROUND

Abdominal fascial closure, e.g., after a surgical procedure involving a laparotomy, laparoscopy and/or other open procedures that involve accessing a patient's abdomen, is a long tedious process and there are currently no automated fascial closure devices available for that use. Currently, after an open procedure, the abdominal fascia wall is closed using a traditional manual suture and needle technique. This manual closure may exert unequal tension on the suture line and allow the suture to buttonhole and/or otherwise cut through the fascia and predispose the patient for an incisional hernia or even a burst abdomen. In addition, due to the additional manipulation of the tissues involved, there is an added risk of infection. The recommended solution to reduce the incidence of Incisional Hernia ("IH") is the small bite technique ("SBT"), which requires very precise suturing technical specs making it difficult to replicate in real day-to-day clinical settings. The SBT is a tedious process and takes substantial amount of time, and so may require the patient to undergo additional anesthesia and utilize already finite precious operative time. Thus, a better way to close the fascia with advanced physical and technological automated technology is needed in open procedures.

Incision hernia is a frequent complication after laparotomy and is associated with high morbidity, decreased quality of life, and high costs. Incidence in high risk patients (e.g., obese individuals (BMI >28), smokers, patients undergoing vascular procedures, colorectal procedures, steroids, and the like) is up to 40%. It is believed that the etiology leading to the development of IH is suture cutting through the fascia due to poor technique causing unequal tension and/or poor tissue perfusion and is not usually due to knot breakdown.

A recent solution is to augment wound closure with a mesh with research claiming such mesh may reduce the incidence of IH to ten percent (10%). However, augmented mesh techniques make the procedure even more technically challenging with lengthier operative time and introduce additional known risk of mesh complications including infection.

Therefore, new devices and methods that facilitate automated fascial wall closure would be useful to reduce the incidence of IH, reduce valuable operative time, and/or perhaps reduce surgical site infection.

SUMMARY

The present invention is directed to medical devices, e.g., during open or laparoscopic surgical procedures, and, more particularly, to devices and methods for closing surgical incisions, e.g., through abdominal fascia after a laparotomy.

The devices, systems, and methods herein generally involve the use of pairs of closure elements, e.g., including double broad-based rectangular/square shaped bio-absorbable contact members, and piercing technology, which may better distribute the forces applied to tissue while closing the fascia, thereby making it less likely to cut through the fascial tissue with subsequently fascial dehiscence culminating in burst abdomen in the acute setting or IH. In addition, the distance between the contact members and/or the distance between the hole and the edge of the contact members may facilitate spacing and distance from the fascial edge of the fasteners directed through the tissue along an incision substantially uniformly, e.g., following the principles of SBT suturing, with the contact members automatically providing the desired spacing, unlike manually using SBT suturing, which increases the risk of user error in the spacing and/or tension applied to the tissue.

In an exemplary method for closing an incision through fascia or other tissue of a subject, a surface of a first closure element including a plurality of contact members, e.g., a pair of contact members formed from relatively large surface area square/rectangular like material, is positioned against tissue from one side of the fascia and a second closure element, e.g., including a corresponding plurality of contact members, is positioned from the other side. One or more fasteners are directed through or from the first closure element, through the tissue, to secure the second closure element against the tissue to close the incision. The closure elements and/or fastener(s) may be formed from bioabsorbable material, e.g., such that the closure elements and fastener(s) may remain within the patient's body after the procedure and dissolve over an extended period of time, e.g., after the fascia has fully healed and regained its strength.

In an exemplary embodiment, the closure elements and fasteners may be delivered via an automated process/stapler device or other delivery tool. In one embodiment, a fastener may be built into or otherwise integral to each contact member of the first closure element, e.g., to fasten using a male to female system. For example, the fastener from each contact member of the first closure element may be directed through the tissue and into or through a corresponding contact member of the second closure element. In exemplary embodiments, the fasteners may include retractable barbs, ratchets, or other male fastener elements that allow the fasteners to easily pierce the fascia and into or through corresponding membranes, holes, or other female fastener elements in the second closure element that prevent the fastener from moving backwards from the second closure element to maintain desired tension. In other embodiments, the fastener may include one or more of a t-fastener, barbed, or zip-tie fastener technology.

In accordance with an exemplary embodiment, a device is provided for closing the fascia of a subject after laparotomy in open procedures that includes one or more pairs of closure elements formed from bioabsorbable material, each closure element comprising a plurality of contact members disposed adjacent one another and one or more links extending between adjacent contact members, each contact member comprising a first surface for placement against tissue adjacent a fascial incision, a second surface opposite the first surface; and one or more fasteners receivable through the contact members when the first surfaces are positioned against tissue on opposite sides of the fascial incision to close the incision.

In accordance with another embodiment, device is provided for closing the fascia of a subject after laparotomy in open procedures that includes one or more pairs of closure elements, each closure element including a plurality of contact members disposed adjacent one another, each contact member comprising a first surface for placement against tissue adjacent an incision, a second surface opposite the first surface; a flexible link integrally formed with and extending between side edges of adjacent contact members; and an aperture extending at least partially between the first and second surfaces of each contact member for receiving a fastener.

In accordance with still another embodiment, a device is provided for closing the fascia of a subject after laparotomy in open procedures that includes a first closure element formed from bioabsorbable material comprising a plurality of contact members disposed adjacent one another and one or more links extending between adjacent contact members, each contact member comprising a first surface for placement against tissue adjacent an incision, a second surface opposite the first surface, and an aperture extending at least partially between the first and second surfaces; and a second closure element formed from bioabsorbable material comprising a plurality of contact members disposed adjacent one another and one or more links extending between adjacent contact members, each contact member comprising a first surface for placement against tissue adjacent an incision, a second surface opposite the first surface, and a male fastener extending from the first surface configured to be received through an aperture of a corresponding contact member in the first closure element.

In accordance with yet another embodiment, an apparatus is provided for a first pair of closure elements formed from bioabsorbable material, each closure element comprising a plurality of contact members disposed adjacent one another and one or more links extending between adjacent contact members, each contact member comprising a first surface for placement against tissue adjacent an incision, a second surface opposite the first surface, and a fastener; and a tool comprising a proximal end including a handle or hub, a distal end including a pair of arms, and an actuator, wherein a closure element of the first pair is carried on each of the arms such that the first surfaces of the closure elements are spaced apart and oriented towards one another such that tissue adjacent an incision may be positioned between the opposing first surfaces, the actuator configured to direct the arms towards one another to direct fasteners from one of the contact elements through the tissue positioned between the first surfaces and engage corresponding fasteners on the other contact element to secure the tissue and close the incision.

In accordance with another embodiment, a method is provided for closing the fascia after laparotomy through tissue of a subject that includes positioning a surface of a first closure element against tissue on a first side of the incision; positioning a surface of a second closure element against tissue on a second side of the incision; and directing a fastener through the first and second closure elements to secure the closure elements against the tissue to close the incision.

In accordance with still another embodiment, a method is provided for closing an incision through tissue of a subject that includes providing first and second closure elements formed from bioabsorbable material, each closure element comprising a plurality of contact members disposed adjacent one another and one or more links extending between adjacent contact members, each contact member comprising a first surface and a second surface opposite the first surface; positioning first surfaces of the contact members of the first closure element against tissue on a first side of the incision; positioning first surfaces of the contact members of the second closure element against tissue on a second side of the incision; and directing fasteners from the contact members of the first closure element through the tissue and corresponding contact members of the second closure element to secure the closure elements against the tissue to close the incision.

Such devices and methods may apply more evenly distributed tension to the tissue being closed and/or may be delivered in less time, e.g., as compared to conventional suturing methods, which may reduce the risk of incisional hernia and/or infection.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features and design elements of the drawings are not to-scale. On the contrary, the dimensions of the various features and design elements are arbitrarily expanded or reduced for clarity. Included in the drawings are the following figures.

DETAILED DESCRIPTION OF THE EXEMPLARY EMBODIMENTS

Before the exemplary embodiments are described, it is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Figure 1:
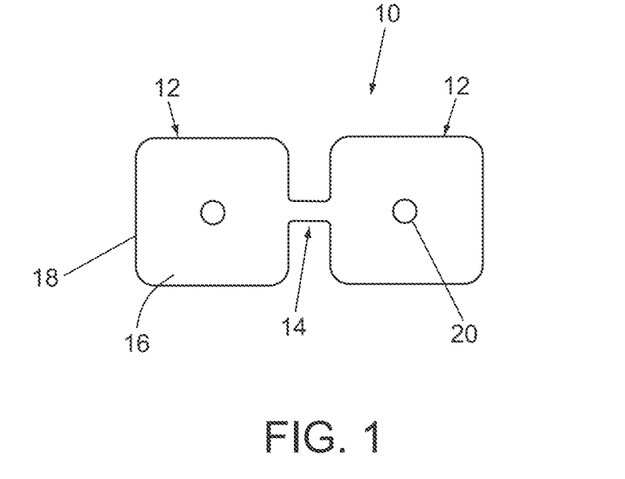
FIG. 1 shows an exemplary embodiment of a closure element including two contact members coupled together by a flexible element.

Turning to the drawings, FIG. 1 shows an exemplary embodiment of a closure element 10 including a pair of contact members 12 coupled together by a link, connector, filament, or other flexible element 14. Each of the contact members 12 includes a first or contact surface 16, e.g., a substantially planar surface for placement against tissue adjacent an incision, and a second surface (not shown) opposite the first surface 16. The contact surface 16 may be substantially smooth or alternatively, the contact surface 16 may be textured and/or include features (not shown) to minimize the contact members 12 from sliding and/or enhance engagement with tissue.

As shown, each contact member 12 has a generally rectangular and/or square shapes, e.g., defining a plurality of (e.g., four) side edges 18, which may be rounded at the corners where the side edges 18 meet, may be rounded and/or beveled between the first and second surfaces, and/or may be otherwise shaped to prevent scratching, catching, or otherwise damaging tissue contacted by the contact members 12. In exemplary embodiments, the side edges 18 of the contact members 12 may have lengths (between adjacent corners) between about three and eleven millimeters (3.0-11 mm) to provide sufficient contact area for the contact surfaces 16. The link 14 may extend from midpoints of corresponding side edges 18, as shown, although alternatively, the link 14 may be offset closer to adjacent corners of the contact members 12, if desired.

In addition, each contact member 12 includes an opening or hole 20 extending between the first surface 16 and the second surface, e.g., to receive one or more fasteners, e.g., sutures, t-fasteners, zip-ties, clips, staples, rivets, connectors extending from other contact members (not shown), and the like, as described elsewhere herein. The hole 20 may have a substantially uniform diameter between the first and second surfaces, e.g., between about one quarter and two millimeters (0.25-2.0 mm), e.g., about one millimeter. Optionally, the hole 20 may be include one more features, e.g., annular ridges, threads, and the like (not shown), which may interact with a fastener received through the hole 20 to enhance engagement. Alternatively, rather than open holes, thin-walled regions or membranes may be provided instead of the holes 20 that may be easily penetrated by fasteners. In another alternative, the holes 20 may have other shapes, e.g., elongated slots, square openings, and the like (not shown), which may accommodate receiving correspondingly shaped fasteners.

Figure 2:
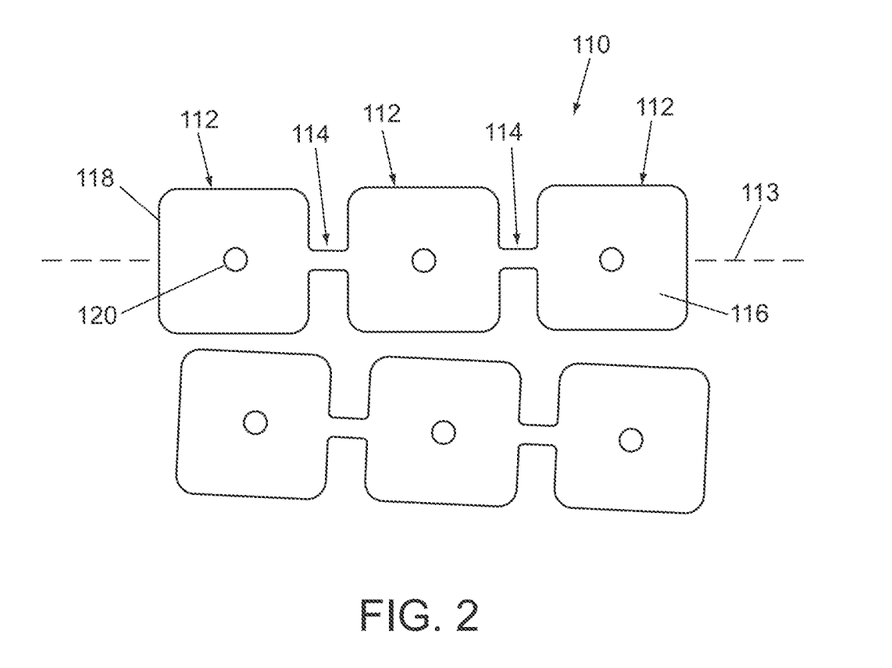
FIG. 2 shows an exemplary embodiment including two pairs of closure elements, each closure element including three contact members coupled together by flexible elements.

Turning to FIG. 2, another embodiment of a closure element 110 is shown that includes three contact members 112 coupled together by flexible links 114, each including an opening or hole 120, e.g., such that the contact members 112 are arranged adjacent one another along an axis 113 or length of the closure element 110 while lying within a common plane. Such a linear arrangement may facilitate positioning the contact members 112 together along the edge of an incision while providing some flexibility in positioning the individual contact members 112 and/or distributing forces in a desired manner, e.g., as described elsewhere herein. As shown, the links 114 extend between adjacent contact members 112, e.g., from midpoints of adjacent side edges 118 and aligned with the axis 113. Alternatively, the links may be offset from but extend substantially parallel to the axis 113, may extend laterally relative to the axis 113, and/or multiple links may be provided that extend between adjacent contact members (not shown).

Figure 3A:
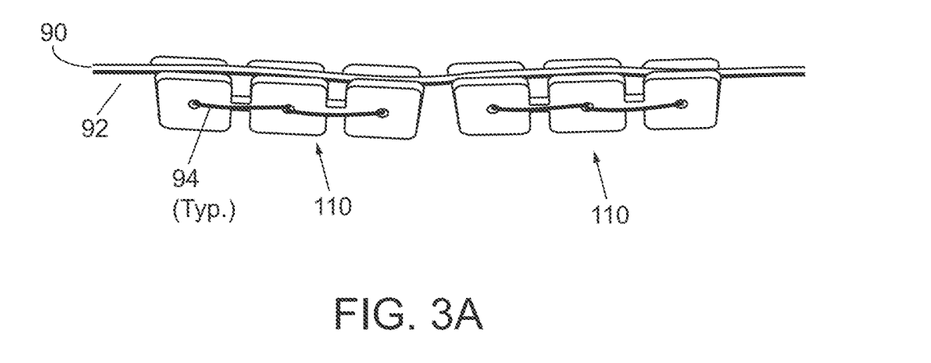
FIGS. 3A and 3B are perspective and side views, respectively, showing an incision through tissue being closed using the closure elements of FIG. 2.
Figure 3B:
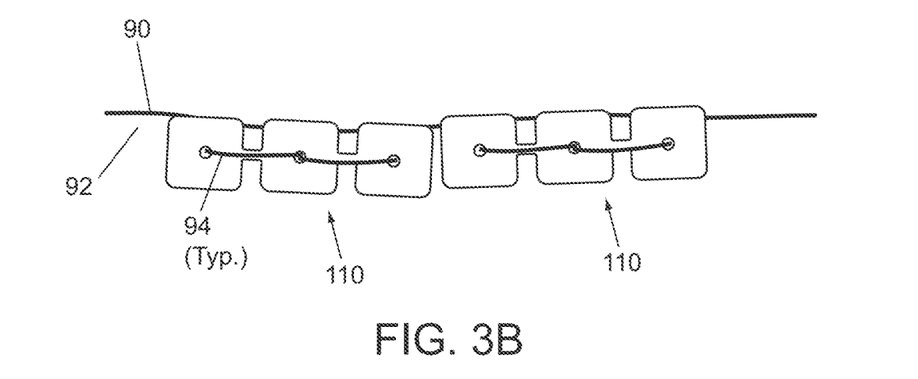

As shown in FIG. 2, the closure elements 110 are generally provided in pairs, e.g., such that the closure elements 110 may be positioned opposite one another along an incision being closed, e.g., as shown in FIGS. 3A and 3B and as described elsewhere herein. Optionally, it will be appreciated that additional contact members may be provided for each closure element, as desired, e.g., such that each closure element includes three, four, five, six, or more contact members with adjacent contact members connected by links (not shown). In addition, although individual contact members are shown as having a substantially square or rectangular shape, it will be appreciated that other shapes may be used having sufficient surface area to contact fascia or other tissue without substantial risk of tearing may be used instead, e.g., circular shapes, octagonal shapes, and the like.

Each closure element 10, 110 (and other closure elements described herein) may be formed from biocompatible material, e.g., plastic, metal, and the like, and/or bioabsorbable material, e.g., poly-lactic acid, poly-glycolic acid, and the like. For example, the contact members and link(s) may be integrally formed together from the same material, e.g., by molding, 3D printing, casting, stamping, and the like. Alternatively, the link(s) may be formed separately and attached to the corresponding edges of the contact members, e.g., by one or more of bonding with adhesive, sonic welding, fusing, and the like. The contact members may be substantially rigid, e.g., defining a substantially planar or other shape, or may be flexible, e.g., biased to a substantially planar or other shape yet sufficiently flexible to conform to a surface to which the contact members are secured.

The contact members and link(s) may have the same, substantially uniform thickness (i.e., distance between the first and second surfaces), e.g., between about one quarter and one millimeter (0.25-1.0 mm), e.g., about 0.5 millimeter. Alternatively, the contact members and link(s) may have different thicknesses, if desired. For example, the link(s) may have a thickness that is thinner than the thickness of the contact members, e.g., if desired to enhance flexibility of the link(s), e.g., between about 0.1-0.5 millimeter, e.g., about 0.25 mm. In addition, the link(s) may have a length (between the adjacent side edges of the contact members between about a half and two millimeters (0.5-2.0 mm), e.g., about one millimeter, depending upon the desired flexibility of the link(s). For example, a relatively short link may provide small flexibility but ensure that the contact members can be manipulated together in a train, while a relatively long link may allow the contact members to be manipulated individually while remaining inseparable. The lengths of the link(s) may also provide a desired spacing distance between adjacent holes in the contact members, e.g., between about five and fifteen millimeters (5.0-15 mm) or between about nine and ten millimeters (9.0-10 mm), depending on the length of the contact members. Consequently, the spacing distance between the holes in the contact members may automatically space the fasteners directed through the tissue via the holes along an incision substantially uniformly. Optionally, multiple links, e.g., two, three, four, or more (not shown), may be provided between adjacent contact members, which may provide flexibility between the contact members but enhance maintaining them in alignment, e.g., when being positioned against tissue and/or otherwise deployed.

FIGS. 3A and 3B show exemplary pairs of closure elements 110 positioned opposite one another along an incision 90, e.g., two pairs of the three-contact member closure elements 110 shown in FIG. 2. A fastener 94 may be delivered through each pair of contact members 110 when the first surfaces 116 are positioned against tissue 92, e.g., on opposite sides of the incision 90 to close the incision 90, as shown and as described elsewhere herein.

Figure 4A:
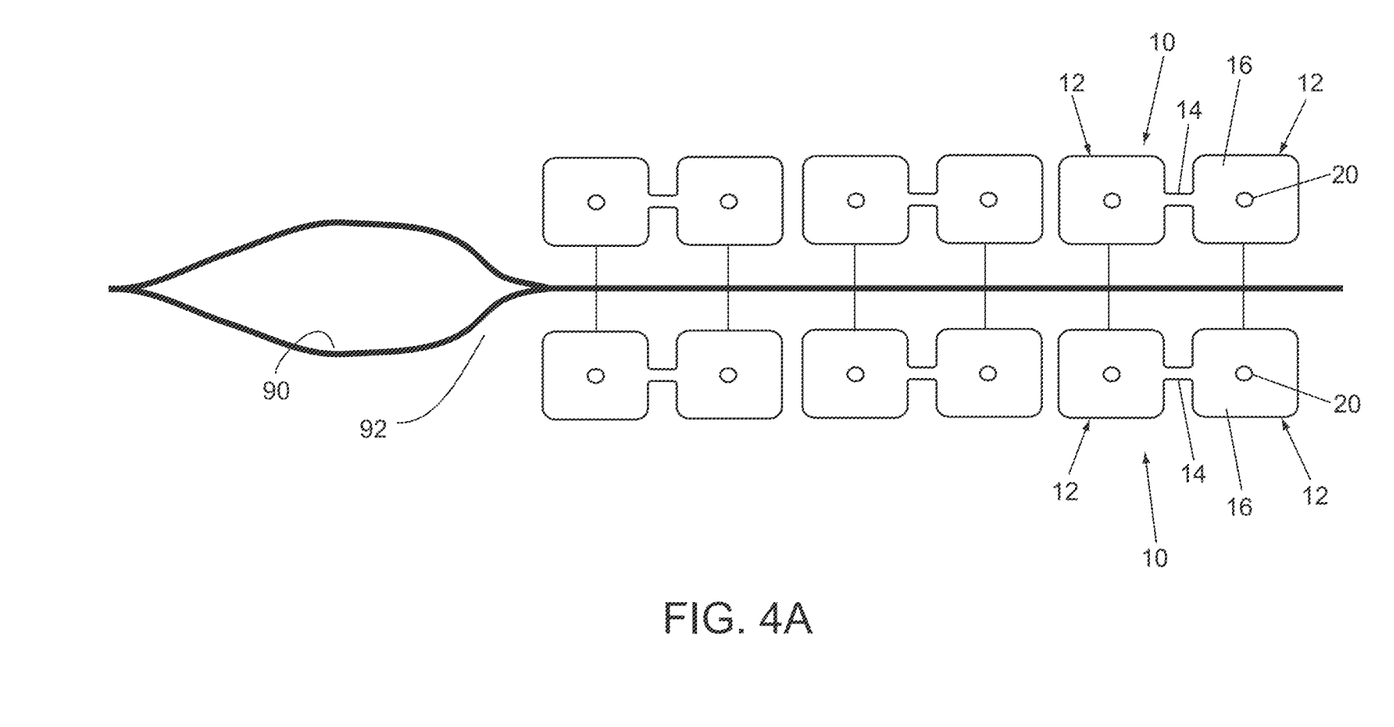
FIGS. 4A and 4B show an exemplary method for closing an incision through tissue a plurality of pairs of closure elements, such as the closure element shown in FIG. 1.
Figure 4B:
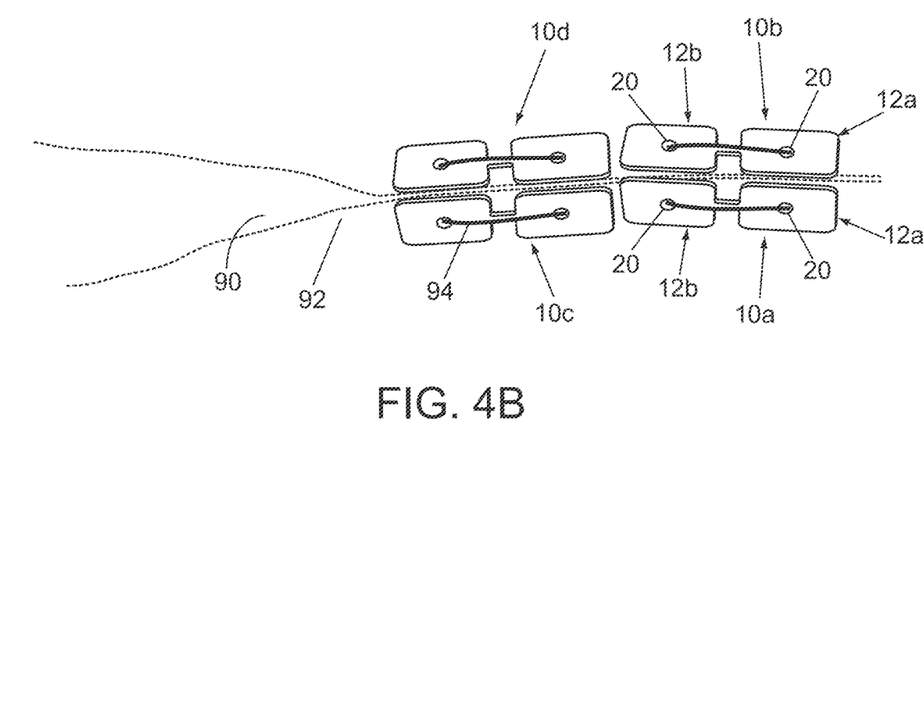

For example, turning to FIGS. 4A and 4B, an exemplary method is shown for closing an incision using pairs of closure elements 10, similar to the closure element 10 shown in FIG. 1. An incision 90 is shown that has been created through tissue 92, e.g., through fascia, skin, and/or other tissue, in order to perform a surgical procedure, e.g., a laparotomy, within a subject's body, e.g., as described elsewhere herein. As shown schematically, in FIG. 4, a set of closure elements 10 may be selected, e.g., including multiple pairs of closure elements 10 sufficient to close the entire length of the incision 90. Each pair of closure elements 10 may be positioned on opposite sides of the incision 90, and tissue 92 along the incision positioned between the contact surfaces 16, e.g., such that the opposite edges of the tissue 92 are engaged between the contact members 12 of the closure elements 10.

One or more fasteners 94 may then be delivered through the opposite holes 20 (or thin-walled regions) of the corresponding contact members 12 on opposite sides of the incision 90. For example, as shown in FIG. 4B, a single suture may be directed through the holes 20 in the first opposite contact members 12a (and through the intervening tissue) and then through the holes 20 in the second opposite contact members 12b (and again through the intervening tissue) to secure the first pair of closure elements 10a, 10b together. This procedure may be repeated for each pair of closure members (10c, 10d shown, others not shown for simplicity) along the incision 90 until the incision is closed. For an incision through fascia, any overlying tissues may also then be closed, e.g., using additional pairs of closure elements or other conventional methods, and the closure elements 10 may remain within the subject's body, e.g., until the incision heals. If the closure elements 10 and fasteners 94 are bioabsorbable, the material should not dissolve until after sufficient time for the incision to adequately heal, e.g., between thirty and sixty days. Alternatively, one or both closure elements 10 and/or the fasteners 94 may not be bioabsorbable and may remain within the subject's body indefinitely.

It will be appreciated that other fasteners may be used instead of sutures to secure the closure elements 10 together. For example, staples or clips (not shown) may be provided that include tines that are spaced apart on opposite ends of a base by a distance corresponding to the distance between the holes 20 in the pair of contact members 12 on each closure element 10. In this embodiment, with reference to FIG. 4B, in an exemplary method, a stapler carrying a staple or clip (not shown) may be positioned such that the tines of a staple may be driven simultaneously through the holes 20 in the first and second contact members 12a, 12b of the first closure element 10a, through the intervening tissue, and then through the holes 20 of the first and second contact members 12a, 12b of the opposite second closure element 10b. The stapler may deform the tines to engage the closure elements 10a, 10b, or the tines may be biased to automatically close and engage the closure elements 10a, 10b. The stapler may include multiple staples that may be delivered sequentially through the pairs of closure elements 10.

Figure 5A:
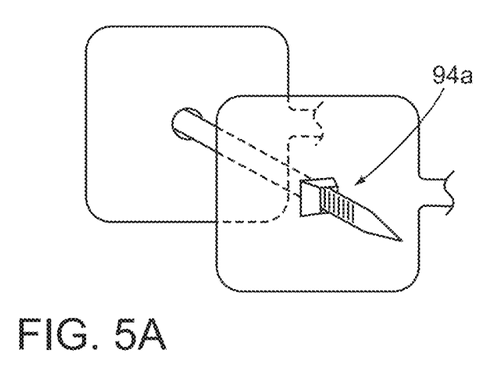
FIGS. 5A-5C show exemplary embodiments of fasteners that may be used to secure closure elements to close an incision.
Figure 5B:
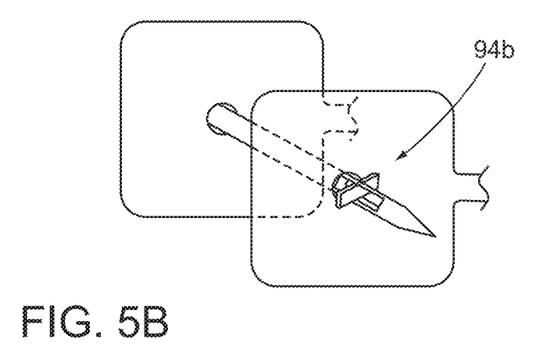
Figure 5C:
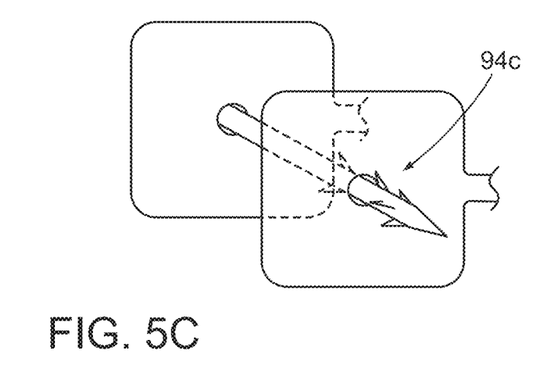

In additional exemplary embodiments, each fastener may include one or more of a zip-tie 94a (e.g., as shown in 5A), a t-fastener 94b (e.g., as shown in FIG. 5B), and/or a barbed or ratcheted fastener 94c (e.g., as shown in FIG. 5C), sized to be received through the holes 20 in the closure elements 10. For example, as shown in FIG. 5A, a shaft of the fastener 94a may be inserted through the holes 20 in opposite contact members 12a, 12b, and then a zip-lock may be advanced down the shaft against the second surface of the contact member 12b to prevent removal of the shaft. Alternatively, a looped zip-tie may be directed through the four holes 20 in the first and second closure elements 10a, 10b shown in FIG. 4B, similar to threading a suture, and then ends of the zip-tie 94a may be engaged, e.g., using cooperating ratchets, detents, or other locking elements (not shown). Optionally, any excess ends may be cut or otherwise separated to provide a lower profile. The t-fasteners 94b and/or barbed fasteners 94c may be directed individually through corresponding pairs of holes 20, e.g., such that separate fasteners may be delivered through first contact members 12a and second contact members 12b shown in FIG. 4B. For example, a tip of a t-fastener 94b may be directed through the holes and then the fastener tip toggled to lock the contact members together. The barbed fastener 94c may include an elongate shaft and a plurality of locking elements (e.g., similar to the fasteners 220 shown in FIG. 6B but including an enlarged head instead of being attached to a contact member), that may be directed through the pair of holes with the locking elements preventing subsequent separation.

Figure 6A:
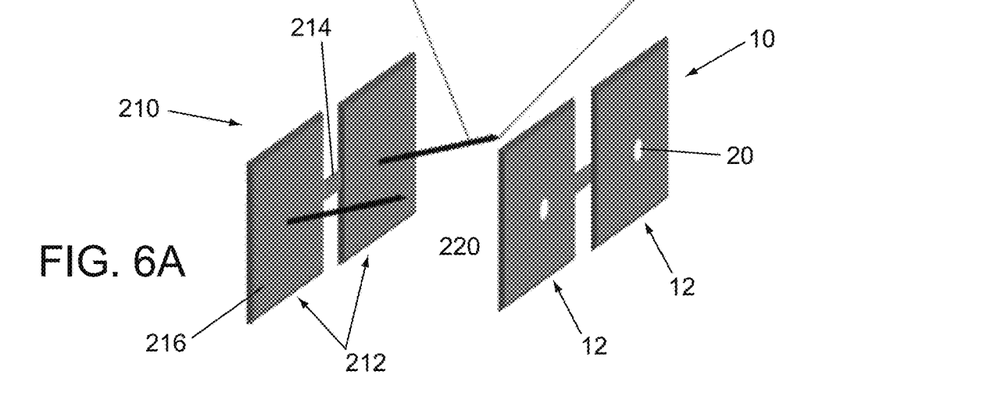
FIG. 6A-6C show additional exemplary embodiments of closure elements that include male/female fasteners.
Figure 6B:
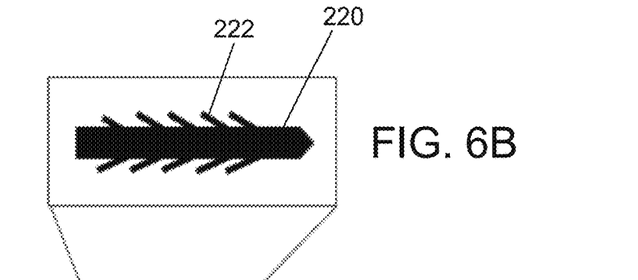

Alternatively, one or more fasteners may be provided integral to one of the closure elements, e.g., to provide a male/female fastener system. For example, as shown in FIGS. 6A and 6B, pairs of closure elements 10, 210 may be provided with the first closure element 10 being a female closure element, e.g., similar to that shown in FIG. 1, and the second closure element 210 including contact members 212 including male fasteners 220. The second closure element 210 may be otherwise constructed similar to other embodiments herein, e.g., with contact members 212 connected by link 214 and each defining a first contact surface 216 configured for placement against tissue adjacent an incision (not shown) and including a fastener 220.

Each fastener 220 may include an elongate shaft extending from the first contact surface 216, e.g., substantially perpendicular to the surface 216 and/or positioned on the surface 216 opposite the hole 20 in the first contact member 20. The male fasteners 220 may be integrally molded with, permanently attached to, or otherwise formed with the second closure element 210, e.g., using similar materials and methods as other embodiments herein.

Figure 6C:
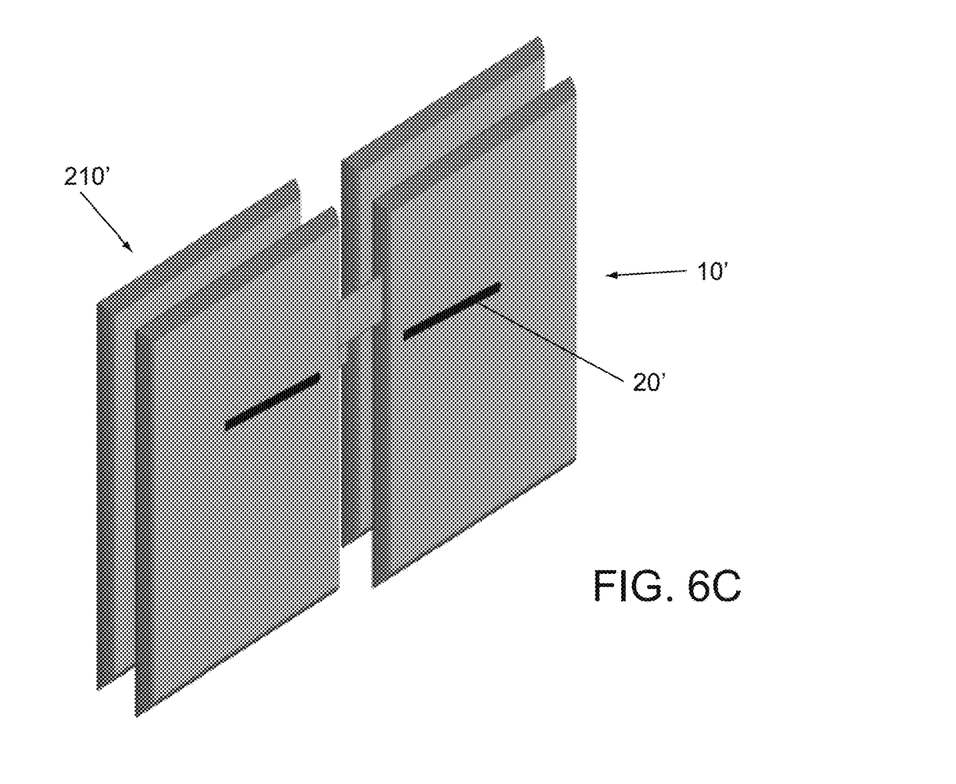

The fasteners 220 may have a diameter or other cross-section slightly smaller than the holes 20 in the first closure element 10 such that the fasteners 220 may be inserted through the holes 20. For example, as shown in FIG. 6B, the fasteners 220 may have a circular cross-section, e.g., corresponding to circular openings 20 in the first closure element 10. Alternatively, as shown in FIG. 6C, closure elements 10', 210' may be provided with the first closure element 10' including an elongate slot 20' and the second closure element 210' including a flat fastener (not shown) that may be received within the slot 20.'

As best seen in FIG. 6B, the fastener 220 may include one or more locking elements, e.g., a plurality of barbs, ratchets, or other elements 222 spaced apart from one another along at least a portion of the fastener 220. For example, the locking elements 222 may include annular ridges including tapered distal surfaces, which may facilitate advancement through tissue and the holes 20, and blunt surfaces that prevent subsequent removal. The fasteners 220 may terminate in a sharpened tip, e.g., to facilitate directing the fasteners 220 directed through the tissue and into or through a corresponding contact member of the second closure element. In exemplary embodiments, the fasteners 220 may be formed from material that is substantially rigid or have sufficient column strength to allow the fasteners 220 to easily pierce fascia or other tissue and pass into or through the holes 20 (or penetrate membranes) in the first closure element 10. Alternatively, the first closure element may include other female fastener receptacles or elements (not shown) that receive the fasteners, yet prevent the fasteners from moving backwards from the first closure element to maintain desired tension.

In an exemplary method for closing an incision through tissue of a subject, similar to other embodiments, a set of multiple pairs of closure elements may be provided corresponding to the length of incision being closed. The contact surface 16 of a first closure element 10 may be positioned against tissue on a first side of the incision, and the contact surface 216 of a second closure element 210 (such as that shown in FIG. 6A) may be positioned adjacent tissue on a second side of the incision. Optionally, the side edges of the contact members 12, 212 may be aligned along the edge of the tissue along the incision, e.g., to space the holes 20, 220 a predetermined, substantially uniform distance from the edge.

With the closure elements 10, 210 positioned opposite one another, the fasteners 220 on the contact members 212 may be directed simultaneously through the tissue and into the holes 20 in the first contact members 12 to secure the closure members 10, 210 against the tissue to close the incision. In this manner, the holes 20 may automatically space the fasteners 220 substantially uniformly along the incision, which may minimize the risk of user error in the spacing and/or tension applied to the tissue to avoid fascial dehiscence or malunion. For example, the incision may extend through a patient's abdominal fascia resulting from a laparotomy, and the closure elements may be secured on opposite sides of the incision to capture tissue between them to close the incision.

Optionally, a tool may be used to deliver one or more fasteners and/or pairs of closure elements. For example, a closure tool device may be provided that includes two contact members (with corresponding openings), and a staple device may be used to deliver a staple including two legs (not shown). The openings and legs may have similar spacing such that the legs of the staple may be delivered simultaneously through the respective openings. Alternatively, individual fasteners may be delivered through individual opposing pairs of holes across the incision, or a suture may be introduced sequentially through each pair of holes.

Figure 7:
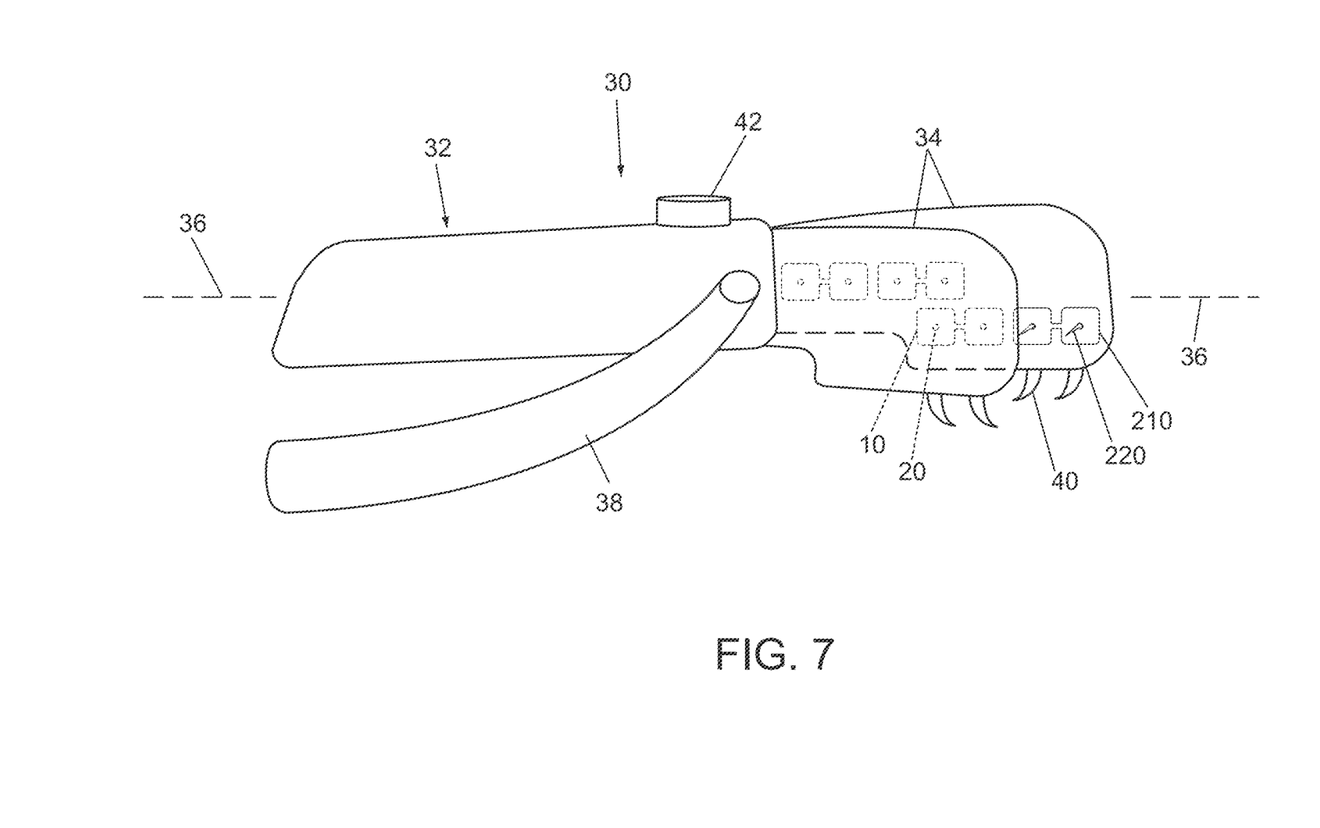
FIG. 7 shows an exemplary embodiment of a delivery tool carrying a plurality of closure elements including male fasteners, e.g., similar to closure elements shown in FIG. 6.

In another alternative embodiment, shown in FIG. 7, a stapler or other delivery tool 30 is shown that may carry one or more closure elements, e.g., a plurality of pairs of closure elements carried by a cartridge (not shown) that may be deployed sequentially from the tool 30. In the embodiment shown, the tool 30 includes a proximal end 32 including a handle or shaft configured to allow a user to hold and/or manipulate the tool 30 during use. A pair of arms 34 extend distally from the proximal end 32 that are spaced apart from one another, e.g., such that the arms 34 are disposed on either side of a central axis 36 aligned with the proximal end 32. The proximal end 32 includes an actuator 38 coupled to the arms 34, e.g., to move the arms laterally towards one another.

Each arm 34 may carry at least one closure element, e.g., a female closure element 10 and a male closure element 210, similar to that shown in FIG. 6A. The arms 34 may include a loading mechanism (not shown) that positions the closure elements 10, 210 on inner surfaces of the arms 34 generally opposite one another. For example, the loading mechanism may advance a pair of closure elements 10, 210 from a cartridge (not shown) carrying a plurality of pairs (additional pair of closure elements shown in phantom in FIG. 7). Alternatively, the tool 30 may be configured to deliver only an individual pair of closure elements 10, 210, e.g., if the tool 30 is single-use or can be reloaded with another pair.

With a first pair of closure elements 10, 210 positioned at the active end of the tool 30, e.g., held opposite one another on the arms 34, the fastener elements 220 on the male closure element 210 are exposed, e.g., to allow them to be oriented towards fascia or other tissue and deployed. The tissue along an incision may be prepared to receive the closure elements 10, 210, and then the contact surface 16 of the first contact element 10 may be positioned against the tissue, e.g., with the fasteners 220 on the opposite side of the tissue. The actuator 38 may then be activated to move the arms 34 towards one another to drive the fasteners 220 through the tissue and into the holes 20 of the female closure element 10, and then release the deployed closure elements 10, 210 secure together and compressing the tissue between them. If the tool carries a plurality of closure elements, the actuator 38 may automatically load an additional pair of closure elements into the active position for delivery upon deployment.

Optionally, the arms 34 may carry one or more hooks or other tissue engaging elements 40 that may be directed at least partially into tissue when the arms 34 are directed towards one another, e.g., to stabilize and/or present the tissue to receive the fasteners 220. Alternatively, the hooks 40 may be movable relative to the arms 34, e.g., such that the hooks 40 may be directed inwardly and/or upwardly before deploying the closure elements 10, 210. For example, a second actuator (not shown) may be provided on the proximal end 32 that may be coupled to the hooks 40 for advancing and/or retracting the hooks 40 independent of the arms 34. In addition or alternatively, a tension gauge 42 may be provided on the tool 30, which may provide an output corresponding to the tension being applied to the fascia, e.g., such that the user may confirm that they apply proper tension to the fascia to avoid fascial dehiscence or malunion.

It will be appreciated that the devices and methods herein may substantially reduce the time to close the abdominal fascia after a surgical procedure, possibly by as much as twenty five percent (25%) compared to conventional SBT suturing techniques, since pairs of closure elements may be delivered rapidly, e.g., simultaneously using a stapler or other tool, such as tool 30. In addition, the devices and methods may also reduce incidence of IH and/or infection at surgical sites, e.g., possibly to ten percent (10%) or less.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. An apparatus for closing an incision after a surgical procedure, comprising:
 a first pair of closure elements formed from bioabsorbable material, each closure element comprising a plurality of contact members disposed adjacent one another and one or more links extending between adjacent contact members, each contact member comprising a first surface for placement against tissue adjacent the incision, a second surface opposite the first surface, and a fastener integral to each contact member; and
 a tool comprising a proximal end including a handle or hub, a distal end including a pair of arms, and an actuator, wherein a closure element of the first pair is carried on each of the arms such that the first surfaces of the closure elements are spaced apart and oriented towards one another such that tissue adjacent the incision may be positioned between the opposing first surfaces, the actuator configured to direct the arms towards one another to direct male fasteners extending from the first surfaces of the contact members of a first closure element of the pair of closure elements through the tissue positioned between the first surfaces and engage corresponding female fasteners in the first surfaces of the contact members on a second closure element of the pair of closure elements to secure the tissue and close the incision,
 wherein the tool carries a cartridge carrying one or more additional pairs of closure elements, and
 wherein the actuator is coupled to an advancement mechanism that moves a second pair of closure elements from the cartridge to the arms after delivering the first pair of closure elements.

2. The apparatus of claim 1, wherein the tool defines a longitudinal axis extending between the proximal and distal ends, and wherein the closure elements are carried on the arms such that the contact members of each closure element are substantially aligned with the longitudinal axis.

3. The apparatus of claim 1, wherein the arms of the tool comprise one or more features that engage tissue between the arms to secure or stabilize the tissue before directing the fasteners through the tissue.

4. The apparatus of claim 1, wherein the first closure element includes a male fastener element integral to and extending from the first surface of each contact member of the first closure element, the male fastener elements configured to engage corresponding female fastener elements on the second closure element when the actuator is actuated to direct the male fastener elements through the tissue.

5. The apparatus of claim 4, wherein each female fastener element is a hole substantially centered on the first surface and extending entirely through the respective contact member between the first and second surfaces.

6. The apparatus of claim 4, wherein the male fastener element is integrally formed with and extending from the first surface of each contact member of the second closure element.

7. The apparatus of claim 4, wherein the male fastener element comprises one or more barbs or ratchet elements to lock the male fastener element once directed through the corresponding female fastener element.

8. The apparatus of claim 1, further comprising a tension gauge on the tool configured to provide an output corresponding to tension being applied to fascia before deploying the closure elements.

9. An apparatus for closing an incision after a surgical procedure, comprising:
 a first pair of closure elements formed from bioabsorbable material, each closure element comprising a plurality of contact members disposed adjacent one another and one or more links extending between adjacent contact members, each contact member comprising a first surface for placement against tissue adjacent a fascial incision, a second surface opposite the first surface;
 one or more fasteners receivable through the contact members when the first surfaces are positioned against tissue on opposite sides of the incision to close the fascia, the one or more fasteners comprising a single fastener integral to each contact member; and
 a tool comprising a proximal end including a handle or hub, a distal end including a pair of arms, and an actuator, wherein a closure element of the first pair is carried on each of the arms such that the first surfaces of the closure elements are spaced apart and oriented towards one another such that tissue adjacent the incision may be positioned between the opposing first surfaces, the actuator configured to direct the arms towards one another to direct the one or more fasteners from one of the closure elements through the tissue positioned between the first surfaces and engage one or more fasteners on the other closure element to secure the tissue and close the incision,
 wherein the tool carries a cartridge carrying one or more additional pairs of closure elements, and
 wherein the actuator is coupled to an advancement mechanism that moves a second pair of closure elements from the cartridge to the arms after delivering the first pair of closure elements.

10. The apparatus of claim 9, wherein each contact member includes an aperture extending at least partially between the first and second surfaces, and wherein the one or more fasteners are configured to be received through the aperture.

11. The apparatus of claim 10, wherein the aperture is a hole extending entirely through the contact member between the first and second surfaces.

12. The apparatus of claim 10, wherein the aperture is a thin-walled region or membrane having a thickness less than a thickness of the contact member between the first and second surfaces.

13. The apparatus of claim 10, wherein each contact member has a single aperture.

14. The apparatus of claim 9, wherein each closure element comprises a pair of contact members coupled together by a flexible link.

15. The apparatus of claim 9, wherein each closure element includes three or more of contact members with adjacent contact members coupled together by flexible links such that contact members are arranged adjacent one another along an axis.

16. The apparatus of claim 9, wherein the one or more fasteners comprise one of a suture, a zip-tie, a t-fastener, and a barbed fastener.

17. The apparatus of claim 9, wherein the first pair of closure elements comprises:
- a first closure element including a plurality of contact members and one or more links extending between adjacent contact members, and wherein the one or more fasteners comprises a female fastener element on each of the contact members; and
- a second closure element including a plurality of contact members and one or more links extending between adjacent contact members, and wherein the one or more fasteners comprises a male fastener element attached to each of the contact members configured to engage a corresponding female fastener element on the first closure element.

18. The apparatus of claim 17, wherein the male fastener element comprises one or more barbs or ratchet elements, and wherein the female fastener element comprises an aperture extending at least partially between the first and second surfaces of each contact member of the first closure element, configured to receive the one or more barbs or ratchet elements to lock the male fastener element to the female fastener element.

19. The apparatus of claim 1, wherein a single fastener is provided on each contact member.

20. The apparatus of claim 19, wherein the single fastener is substantially centered on the first surface of each contact member.

21. The apparatus of claim 9, wherein the single fastener is substantially centered on the first surface of each contact member.

* * * * *